United States Patent [19]

Lowack et al.

[11] Patent Number: 5,523,420
[45] Date of Patent: Jun. 4, 1996

[54] PREPARATION OF ALPHA-TOCOPHEROL AND ALPHA-TOCOPHERYL ACETATE IN LIQUID OR SUPERCRITICAL CARBON DIOXIDE

[75] Inventors: Rainer Lowack, Mannheim; Joachim Meyer, Maxdorf; Manfred Eggersdorfer, Frankenthal; Paul Grafen, Weisenheim, all of Germany

[73] Assignee: BASF Aktiengesellschaft, Ludwigshafen, Germany

[21] Appl. No.: 439,762

[22] Filed: May 12, 1995

Related U.S. Application Data

[63] Continuation of Ser. No. 167,053, Dec. 16, 1993, abandoned.

[30] Foreign Application Priority Data

Dec. 22, 1992 [GB] United Kingdom ............... 42 43 464

[51] Int. Cl.$^6$ ........................................ C07D 311/72
[52] U.S. Cl. ........................................ 549/411
[58] Field of Search ........................................ 549/411

[56] References Cited

U.S. PATENT DOCUMENTS 3,444,213  5/1969  Nelan ........................ 549/411
4,217,285  8/1980  Yoshino et al. ............. 549/411

FOREIGN PATENT DOCUMENTS 100471   2/1984  European Pat. Off. .
2602772  2/1988  France .
2743920  3/1978  Germany .
222170   9/1942  Switzerland .

OTHER PUBLICATIONS

Separation of Tocopherols from Deodorizers . . . , Brunner et al., The Journal of Supercritical Fluids, 1991, 4, 72–80.

Diploma theses of Martin Unterhuber, Univ. Erlangen–Nurnberg, Apr. 1986.

*Primary Examiner*—Nicky Chan
*Attorney, Agent, or Firm*—Keil & Weinkauf

[57] ABSTRACT

A process for preparing α-tocopherol or tocopheryl acetate by cyclocondensation of trimethylhydroquinone with phytol or isophytol in the presence of an acid catalyst and of a solvent and, where appropriate, subsequent acetylation, which comprises carrying out the cyclocondensation and, where appropriate, the subsequent acetylation in liquid or supercritical carbon dioxide as solvent.

5 Claims, No Drawings

PREPARATION OF ALPHA-TOCOPHEROL AND ALPHA-TOCOPHERYL ACETATE IN LIQUID OR SUPERCRITICAL CARBON DIOXIDE

This application is a continuation of U.S. application Ser. No. 08/167,053, filed on Dec. 16, 1993, abandoned.

The present invention relates to a process for preparing α-tocopherol or α-tocopheryl acetate by cyclocondensation of trimethylhydroquinone with phytol or isophytol in the presence of an acid catalyst and of an inert solvent and, if required, subsequent acetylation.

Because of the continually increasing demand for α-tocopherol (vitamin E), its preparation by the above-described cyclocondensation has been investigated by many vitamin producers. Thus, numerous patents describe cyclocondensation processes which differ essentially in the nature of the acid catalyst or in the choice of the solvents. Examples of acid catalysts described are mixtures of strong acids and Lewis acids, such as HCl and $ZnCl_2$ (cf. EP 100 471; JP-A2-226 976/87; JP-A2-54380/85), acid ion exchangers (cf. JP-A-77 064/78), $SiO_2/Al_2O_3$ pretreated with protic acids (cf. DE 27 43 920 and DE 24 04 621), trifluoroacetic acid or its anhydride (cf. EO 12824), certain complexes of $AlCl_3$ or $BF_3$ (cf. DE 19 09 164) or $BF_3$ in acetic acid (cf. U.S. Pat. No. 3,444,213).

Examples of solvents which have been used are hydrocarbons such as heptane, halohydrocarbons, ketones, acetic acid and, in particular, alkyl acetates.

The water produced in the cyclocondensation of trimethylhydroquinone and isophytol is however removed by azeotropic distillation or bound by hygroscopic substances such as $ZnCl_2$ and gaseous hydrogen chloride in the form of an aqueous phase which separates out.

The disadvantages of the known processes are that the workup of the reaction mixture and the purification of the tocopherol or tocopheryl acetate on the industrial scale are rather costly. Thus, the resulting crude α-tocopherol or α-tocopheryl acetate must in most of the processes finally be purified by distillation under greatly reduced pressure, which is very costly in terms of the energy and apparatus required and leads to losses of yield because of the temperatures exceeding 200° C. which are required.

According to recent investigations by G. Brunner et al. in The Journal of Supercritical Fluids 4 (1991) 72–80, the diploma thesis of Martin Unterhuber, University Erlangen-Nuremberg, April 1986, and FR 2 602 772, it is possible to purify both α-tocopherol and tocopheryl acetate by distraction in supercritical carbon dioxide. The principle of distraction is described by K. Zosel in Angewandte Chemie 90 (1978) 748–55, Intern. Ed. in Engl, 17 (1978) 702–709. Distraction is a combination of extraction or fractionating extraction with liquid or supercritical carbon dioxide and fractionating distillation of the extract in liquid or supercritical carbon dioxide.

To use the purification method for synthetic α-tocopherol, it would be necessary first to remove the organic solvent employed in the synthetic reaction in the previously disclosed process for tocopherol or tocopheryl acetate before carrying out the purification.

It is an object of the present invention to improve the preparation of α-tocopherol or α-tocopheryl acetate by cyclocondensation of trimethylhydroquinone with phytol or isophytol in the presence of an acid catalyst and, where appropriate, subsequent acetylation so that the workup of the reaction mixture and the purification of the product is more advantageous on the industrial scale.

We have found that this object is achieved by a process for preparing α-tocopherol or α-tocopheryl acetate by cyclocondensation of trimethylhydroquinone with phytol or isophytol in the presence of an acid catalyst and of a solvent and, where appropriate, subsequent acetylation, which comprises carrying out the cyclocondensation and, where appropriate, the subsequent acetylation in liquid or preferably supercritical carbon dioxide as solvent.

Supercritical carbon dioxide is physiologically innocuous, a good solvent for phytol, isophytol and the reaction products and has a low critical temperature of only 31° C. and a low critical pressure and is thus a good solvent for the cyclocondensation of trimethylhydroquinone and isophytol to α-tocopherol and, where appropriate, subsequent acetylation thereof.

The process is particularly advantageous when ethane, propane or butane, preferably propane, is added in amounts of about 10–50% by weight, preferably 15–30% by weight, as cosolvent to the liquid or, preferably, supercritical carbon dioxide. The alkane acts as entrainer during subsequent distraction.

The addition of ethane (critical temperature 32° C.), propane (critical temperature 97° C.) or butane (critical temperature 136° C.) considerably increases the dissolving power of supercritical $CO_2$ and greatly reduces the viscosity of the reaction mixture. The mixtures of $CO_2$ and propane which are preferably used according to the invention are in the supercritical state at temperatures above 31° C. and under pressures above 65 bar. The properties of the mixture are comparable to those of the pure supercritical substances.

The process according to the invention is also very advantageous when the cyclocondensation and, where appropriate, the subsequent acetylation are carried out in supercritical carbon dioxide to which up to 10% by weight of acetic acid has been added.

The tocopherol synthesis according to the invention is carried out by bringing about the cyclocondensation of trimethylhydroquinone and phytol or isophytol in liquid or supercritical $CO_2$ or a $CO_2$/ cosolvent mixture. Since the critical temperature of $CO_2$ is only 31° C., cyclocondensation is preferably carried out in supercritical $CO_2$. If liquid $CO_2$ is used, i.e. at temperatures below 31° C., it would be necessary to employ particularly active catalysts such as boron trifluoride or aluminum trichloride.

Acid catalysts which can be used for the cyclocondensation are essentially all acid catalysts known for this reaction, i.e. Lewis acids such as zinc chloride, alumosilicates, zeolites or montmorillonites, or Bronsted acids such as acid ion exchangers, toluenesulfonic acids, methanesulfonic acid, trifluoromethanesulfonic acid, trifluoroacetic acid, sulfuric acid, hydrochloric acid, or sulfonated active carbon or else combinations of these acids.

Particularly advantageous acid catalysts are acid ion exchangers or similar heterogeneous catalysts such as sulfonated active carbon or alumosilicates, because no aqueous phase is formed when they are used, with no need to remove the water of reaction by distillation, which considerably simplifies the process. The water formed in the reaction can be removed after the cyclocondensation, with regeneration (drying) of the catalyst, for example by adding acetic anhydride.

Particularly suitable acid ion exchangers are strongly acid ion exchangers based on polystyrene and containing —$SO_3H$ groups in the $H^+$ form. Examples which may be mentioned are Amberlite® IR 112 and 120 (Rohm & Haas), Dowex® 50 (DOW Chemicals), Lewatit® S 100 (Bayer), Permutit® Q and RS (Permutit Co.), Wofatit® KPS 200

(Farbenfabrik Wolfen), Zeocarb® 225 (Permutit Co.) and, in particular, Amberlyst® A 15 (Rohm & Haas).

It is possible, if required, to prepare α-tocopheryl acetate from the tocopherol by subsequent addition of an acetylating agent such as acetic anhydride without replacing the solvent and catalyst.

Both the cyclocondensation and acetylation are generally carried out at from 25° to 220° C., preferably from 90° to 120° C. and under from 50 to 300 bar, preferably from 80 to 200 bar.

The reaction times are generally from about 1 minute to 2 hours, preferably from about 10 minutes to 1.5 hours.

The carbon dioxide is generally used in amounts of from 2 g to 30 g, preferably from 5 g to 20 g, per g of trimethylhydroquinone.

Use of cosolvents correspondingly reduces the amount of carbon dioxide required.

The solution, which is obtained according to the invention, of α-tocopherol or α-tocopheryl acetate in liquid or supercritical $CO_2$ or in the supercritical mixture of $CO_2$ and the cosolvent can subsequently be purified by distraction in this solvent or solvent mixture immediately, i.e. without the need to replace the solvent. Purification of α-tocopheryl acetate by distraction from supercritical $CO_2$ is described in FR 2 602 772. It is essentially based on the difference in solubility of the low-boiling by-products, of α-tocopherol or α-tocopheryl acetate and the higher boiling by-products in supercritical gas and by isolation of the by-products or the required product by reducing the pressure of the resulting fractions to atmospheric or else by increasing the temperature while keeping the pressure constant. This is generally carried out at about 35°–90° C. under about 80 to 250 bar. Further details of the distraction of α-tocopherol and α-tocopheryl acetate are to be found in FR 2 602 772 and the diploma thesis of M. Unterhuber cited above.

Combination of the process according to the invention with the purification of the crude α-tocopherol or α-tocopheryl acetate by distraction from supercritical $CO_2$ or a supercritical mixture of $CO_2$ and, in particular, propane and butane makes it possible to carry out the cyclocondensation of trimethylhydroquinone with phytol or isophytol and, where appropriate, the subsequent acetylation, and the working up of the reaction mixture and the purification of the product in a particularly advantageous way.

EXAMPLE 1

15.02 g (98.8 mmol) of trimethylhydroquinone and 10.59 g of the strongly acid ion exchanger Amberlyst® A15 were placed in a 300 ml autoclave, and 116 g of $CO_2$ were condensed in. Heating to 100° C. resulted in a pressure of 185 bar. 37.80 ml (29.48 g; 99.6 mmol) of isophytol were injected by means of an HPLC pump over the course of 1.5 hours (h) at 108° C. After stirring at 108° C. for a further 30 minutes (min), the autoclave was cooled to room temperature (RT), and the pressure was released. The ion exchanger was removed from the product by centrifuging the mixture. The 48.9 g of isolated pale yellow oil contained 83% tocopherol, which corresponds to an 84% yield of pure α-tocopherol.

EXAMPLE 2

14.92 g (98.2 mmol) of trimethylhydroquinone and 4.51 g of the strongly acid ion exchanger Amberlyst® A15 were placed in a 300 ml autoclave, and 105 g of $CO_2$ were condensed in. Heating to 90° C. resulted in a pressure of 165 bar. 37.90 ml (99.9 mmol) of isophytol were injected by means of an HPLC pump over the course of 1.5 h at 90° C. After stirring at 90° C. for a further 30 min, 26.1 ml of acetic anhydride were pumped in over the course of 5 min. After 4 h, the autoclave was cooled to RT and the pressure was released. The ion exchanger was removed from the product by centrifuging the reaction mixture or, after it had been dissolved in heptane, by filtration. Yield after distillation 31.0 g (68%) of a pale yellow oil with a tocopheryl acetate content of more than 98%.

EXAMPLE 3

15.12 g (99.38 mmol) of trimethylhydroquinone and 4.89 g of zinc chloride were placed in a 300 ml autoclave, and 3 bar of gaseous hydrogen chloride were injected, and 118 g of $CO_2$ were condensed in. Heating to 110° C. resulted in a pressure of 175 bar. 37.80 ml (99.9 mmol) of isophytol were injected by means of an HPLC pump over the course of 1.5 h at 90° C. After stirring at 110° C. for a further 30 min, the autoclave was cooled to RT and the pressure was released. The catalyst was removed from the reaction mixture by taking it up in heptane and washing with aqueous methanol and then water. The yield based on pure tocopherol was 23.12 g, corresponding to 55% of theory.

We claim:

1. A process for preparing α-tocopherol or tocopheryl acetate by cyclocondensation of trimethylhydroquinone with phytol or isophytol in the presence of an acid catalyst and of a solvent and, optionally, subsequent acetylation, which comprises carrying out the cyclocondensation and, optionally, the subsequent acetylation in liquid or supercritical carbon dioxide as solvent.

2. A process as claimed in claim 1, wherein the cyclocondensation and, optionally, the subsequent acetylation are carried out in supercritical carbon dioxide.

3. A process as claimed in claim 1, wherein the cyclocondensation and, optionally, the subsequent acetylation are carried out in liquid or supercritical carbon dioxide to which from 10 to 50% by weight of ethane, propane or butane has been added as cosolvent.

4. A process as claimed in claim 2, wherein the cyclocondensation and, optionally, the subsequent acetylation are carried out in supercritical carbon dioxide to which from 15 to 30% by weight of propane or butane has been added as cosolvent.

5. A process as claimed in claim 1, wherein the cyclocondensation and, optionally, the subsequent acetylation are carried out in liquid or supercritical carbon dioxide to which up to 10% by weight of acetic acid has been added as cosolvent.

* * * * *

UNITED STATES PATENT AND TRADEMARK OFFICE
CERTIFICATE OF CORRECTION

PATENT NO.: 5,523,420

DATED: June 4, 1996

INVENTOR(S): LOWACK et al.

It is certified that error appears in the above-identified patent and that said Letters Patent is hereby corrected as shown below:

On the Title page, item [30],
  "[GB]  United Kingdom" should read
  --DE   Germany--.

Signed and Sealed this

Sixth Day of August, 1996

Attest:

BRUCE LEHMAN

Attesting Officer

Commissioner of Patents and Trademarks